United States Patent
Karstens

(10) Patent No.: US 6,999,046 B2
(45) Date of Patent: Feb. 14, 2006

(54) SYSTEM AND METHOD FOR CALIBRATING LOW VISION DEVICES

(75) Inventor: Christopher K. Karstens, Apex, NC (US)

(73) Assignee: International Business Machines Corporation, Armonk, NY (US)

( * ) Notice: Subject to any disclaimer, the term of this patent is extended or adjusted under 35 U.S.C. 154(b) by 652 days.

(21) Appl. No.: 10/125,660

(22) Filed: Apr. 18, 2002

(65) Prior Publication Data
US 2003/0197693 A1    Oct. 23, 2003

(51) Int. Cl.
G09G 5/00    (2006.01)

(52) U.S. Cl. .............................. 345/7; 349/11; 832/254

(58) Field of Classification Search .................. 345/7, 345/8, 9; 349/11; 382/254, 114; 351/211; 832/254, 114
See application file for complete search history.

(56) References Cited

U.S. PATENT DOCUMENTS 5,223,865 A * 6/1993 Shirao et al. ............... 351/243
5,359,675 A * 10/1994 Siwoff ........................ 382/114
5,777,715 A * 7/1998 Kruegle et al. ............. 351/158
5,825,340 A * 10/1998 Torizuka et al. ............... 345/8
5,831,667 A * 11/1998 Siminou ...................... 348/63
5,838,422 A   11/1998 Caskey ....................... 351/223
5,953,101 A    9/1999 Nordquist ................... 351/211
6,322,545 B1  11/2001 Schachar .................... 604/294

* cited by examiner

Primary Examiner—Regina Liang
Assistant Examiner—Jennifer T. Nguyen
(74) Attorney, Agent, or Firm—Van Leeuwen & Van Leeuwen; Gerald R. Woods

(57) ABSTRACT

A system and method for calibrating low vision devices is presented. Image processing presents views that include information based upon a user's vision impairment. The user provides feedback corresponding to the views and image processing generates calibration settings based upon the user's feedback. The user selects which calibration setting to load into a vision enhancement device and also whether to load the calibration settings onto a removable storage device for use in other vision enhancement devices. The user is able to reconfigure the vision enhancement device using previously generated calibration settings or the user may generate new calibration settings based upon the condition of his vision impairment.

15 Claims, 9 Drawing Sheets

SYSTEM AND METHOD FOR CALIBRATING LOW VISION DEVICES

BACKGROUND OF THE INVENTION

1. Technical Field

The present invention relates in general to a system and method for calibrating a low vision device. More particularly, the present invention relates to a system and method for using a series of calibration steps to customize a low vision device for a user.

2. Description of the Related Art

Low vision is a term given to impairments that make it affect the ability of a person to correctly see objects. Low vision may include minor impairments such as color blindness, or a severe impairment such as macular degeneration.

Macular degeneration is a term used to refer to a group of disorders that affect the central portion of the retina and, as a result, the central vision. The most common forms of macular degeneration usually affect patients over the age of 65. These forms, which are often called "age-related macular degeneration", are collectively the most common cause of legal blindness in developed countries. Age related macular degeneration is extremely prevalent with as many as one in ten patients over the age of 65 affected to some degree.

The inside of the eye is lined by three layers of tissue which each have a critical role in normal vision. The three layers are the retina, the retinal pigment epithelium (RPE), and the choroid. The retina is the first layer struck by light as it enters the eye and consists of a complex network of nervous tissue called photoreceptors. Photoreceptors convert light into electrical signals that are then amplified and processed by other cells before being sent to the brain through an optic nerve. The central part of the retina, called the macula, has a number of special structural features that allow images to be seen with very high resolution.

The retinal pigment epithelium (RPE) is the middle tissue layer of the eye and is one cell thick. The RPE provides metabolic support for photoreceptor cells and also removes old bits of cellular debris from the tips of the photoreceptor cells as they renew themselves. The choroid is the third tissue layer that is a rich network of blood vessels. These blood vessels supply oxygen and nutrients to the RPE and photoreceptor cells.

In macular degeneration, clumps of yellowish cellular debris, possibly of retinal origin, gradually accumulate within and beneath the RPE. These deposits are visible to a clinician looking inside the eye as small yellow dots known as drusen. With the passage of time, patches of RPE cells may die from the accumulating debris. As a result, bare spots form in the RPE that are referred to as "geographic atrophy". RPE areas with geographic atrophy stop providing metabolic support to overlying photoreceptor cells. In turn, the overlying photoreceptor cells seize functioning which brings about vision loss in the corresponding retina area.

Although reduced central or reading vision is most common, low vision may also result from decreased side (peripheral) vision, or a loss of color vision. In addition, low vision may result in a person losing the ability to adjust to light, contrast or glare. Vision assistance devices are available for people with low vision issues. These devices are typically scanners or cameras connected to a head mounted display (HMD) or closed circuit television (CCTV). Low vision devices generally provide magnification, basic focus, and contrast features that enable a low vision user to see words, a person's face, and objects. A challenge found with existing low vision devices is that they do not provide image-processing functions for increased image enhancement. For example, a low vision device may not distinguish specific colors to a person that is colorblind. What is needed, therefore, is a way to customize a low vision device corresponding to the type and state of a user's vision impairment.

SUMMARY

It has been discovered that image processing allows a user to configure a low vision device to display an image based upon the user's particular vision impairment. Image processing sequences through a series of calibration steps and generates calibration settings based upon user input received during the calibration steps.

One of the user's eyes is covered and the user selects one or more calibration steps corresponding to vision impairments of the uncovered eye. For example, calibration steps may be selected for low vision artifacts, color impairments, or contrast impairments. When the user selects a calibration step, image processing displays one or more views corresponding to the calibration step. The user is prompted to provide feedback corresponding to the displayed view. Using the example described above, the calibration step may focus on a color impairment (colorblindness) and the user is prompted to select which colors he is not able to distinguish. Image processing generates calibration settings based upon the user's feedback.

After the user steps through his selected calibration steps, the user is queried as to whether he wishes to calibrate his second eye. If the user chooses to calibrate his second eye, the user's second eye is uncovered and his first eye is covered. Once covered, image processing prompts the user to select one or more calibration steps corresponding to vision impairments of his second eye.

After calibration steps are completed, the user selects which calibration settings should be loaded into a vision enhancement device. Image processing loads the selected calibration settings into the vision enhancement device, and the user is prompted as to whether to load the calibration settings into a removable storage area, such as a smart card. For example, the user may have multiple vision enhancement devices in which he wishes to load calibration settings. The user may reconfigure the vision enhancement device at any time using existing calibration settings or the user may step through calibration steps to generate additional calibration settings based upon the condition of his vision impairment.

While this invention may be used in conjunction with traditional scanners, cameras mounted to a head mounted display (HMD), or closed circuit television (CCTV), these devices are not needed to use the calibration system and method described herein. This invention is able to calibrate any display and is not dependent on a scanner or camera to operate. For example, the calibration method may be used by a colorblind person viewing a presentation file on a notebook computer, in which case the notebook computer display is used as the display device. In addition, a television set can be calibrated using the methods provided herein, in which case the television set acts as the low vision display device.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings. The use of the same reference symbols in different drawings indicates similar or identical items.

DETAILED DESCRIPTION

The following is intended to provide a detailed description of an example of the invention and should not be taken to be limiting of the invention itself. Rather, any number of variations may fall within the scope of the invention which is defined in the claims following the description.

Figure 1:
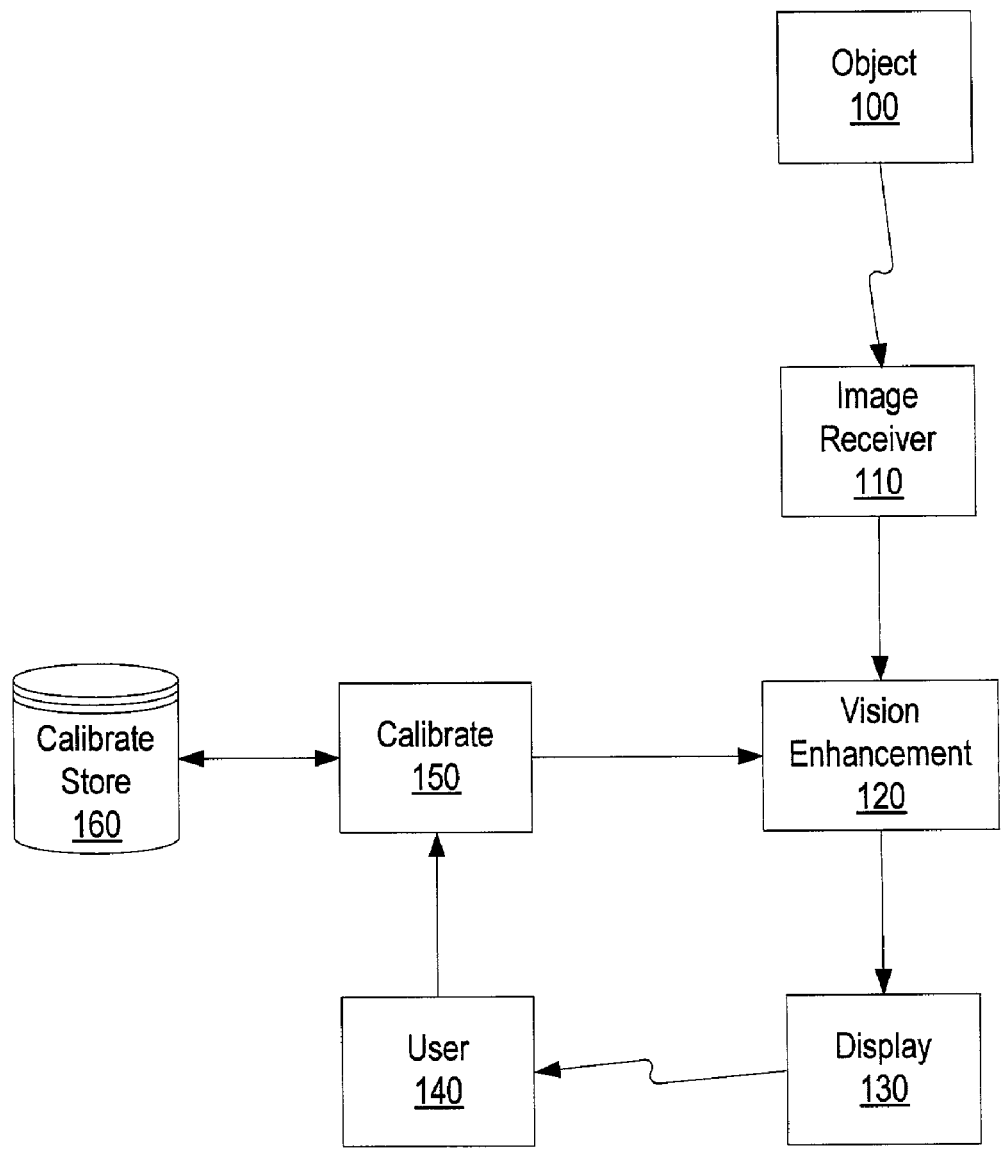
FIG. 1 is a diagram showing a user calibrating an vision enhancement device to better view an object on a display.

FIG. 1 is a diagram showing a user calibrating a vision enhancement device corresponding to his particular vision impairment. User 140 performs calibration steps using calibrate 150 to generate specific calibration settings corresponding to user 140's vision impairment (see FIG. 2 and corresponding text for further details regarding calibration steps). For example, user 140 may have a vision spot impairment on the left side of his viewing area (see FIG. 3 and corresponding text for further details regarding vision spots). Calibrate 150 manages the calibration steps and stores user 140's response to the calibration steps in calibration store 160. For example, calibrate 150 may be an automated vision calibration system in which user 140 sits at and uses a keyboard and mouse to navigate through various calibration steps.

Calibrate 150 generates calibration settings corresponding to user 140's calibration inputs. Using the example described above, calculate 150 may generate multiple views to mask the vision spot impairment. Calibrate 150 loads the calibration settings in vision enhancement 120. Vision enhancement 120 may be a device capable of using calibration settings to alter an image. For example, vision enhancement 120 may be a front-end processing system of a Head Mounted Display (HMD). Once the calibration settings are loaded, vision enhancement 120 is ready to receive images and adjust the images corresponding to the calibration settings.

Image receiver 110 captures a depiction of object 100 for vision enhancement 120 to further process. Image receiver 110 may be a device capable of capturing images, such as a video camera. Image receiver 110 sends the depiction to vision enhancement 120 for processing. For example, image receiver 110 may be a digital video camera and the depiction may be sent to vision enhancement 120 using a IEEE-1394 connection.

Vision enhancement 120 receives the depiction and alters the depiction corresponding to the calibration settings. Using the example described above, vision enhancement 120 may "black out" the left side of the depiction and send the altered image to display 130. Display 130 shows the altered image on a screen for user 140 to view. User 140 may re-configure vision enhancement 120 as desired for various conditions, such as daytime and nighttime. In one embodiment, a system may include an image receiver, a vision enhancement, and a display for each eye, such as a HMD.

Figure 2:
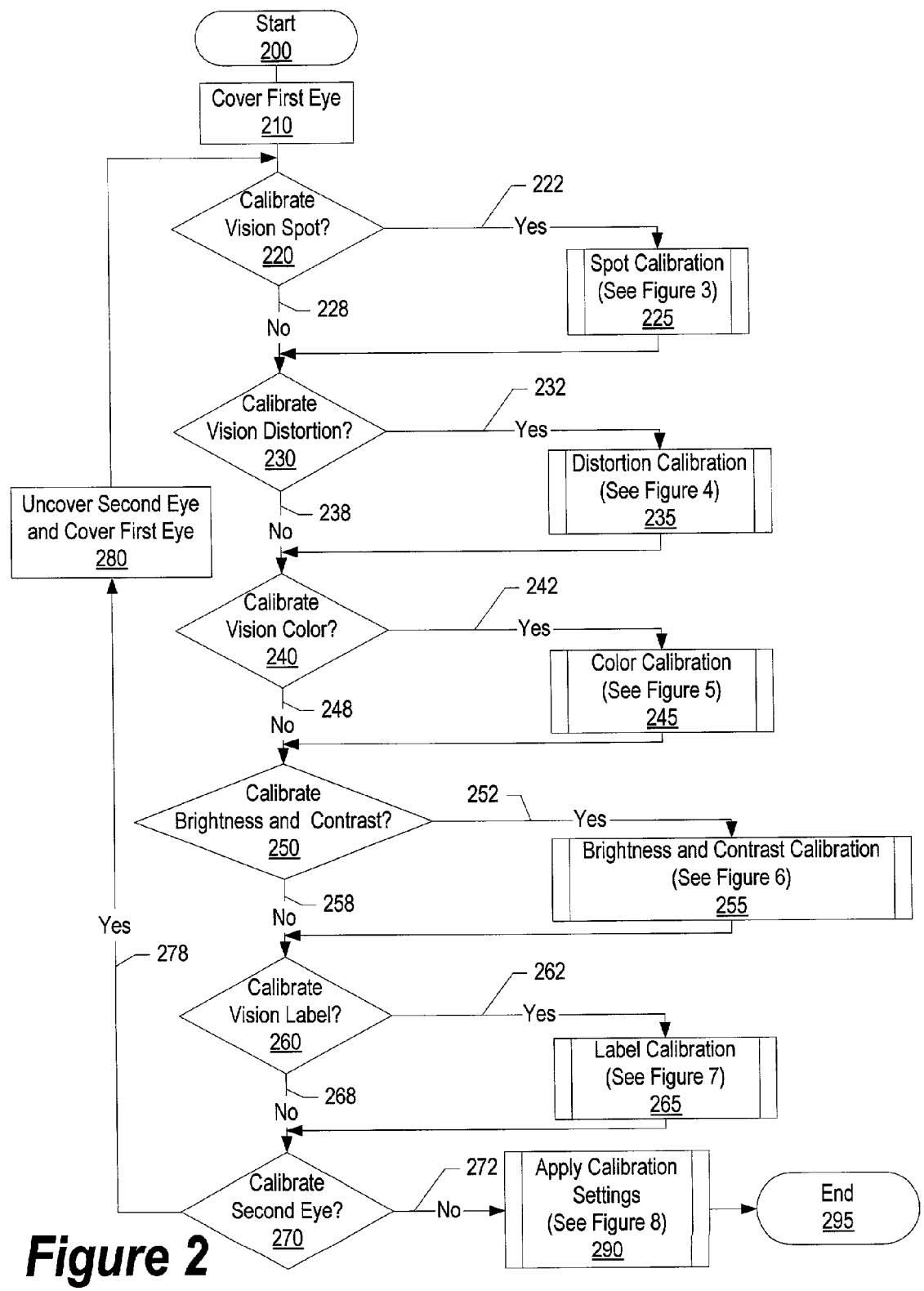
FIG. 2 is a high-level flowchart showing steps taken in calibrating an image enhancement device.

FIG. 2 is a high-level flowchart showing steps taken in calibrating a vision enhancement device. Processing starts at 200, whereupon one of the user's eye is covered. For example, the eye may be covered manually with the user's hand. Another example is that the eye may be covered using an automated process, such as with a vision device moving an obstruction (i.e. metal plate) over the user's eye to block his vision. Still another example is that a corresponding display may be turned off if a person is using an HMD.

A determination is made as to whether to calibrate an enhancement device for vision spot (decision 220). For example, a user may have an impairment in one eye in which he is not able to see certain areas (spots). If the enhancement device should be calibrated for vision spot for the particular eye, decision 220 branches to "Yes" branch 222 whereupon vision spot calibration occurs (pre-defined process block 225, see FIG. 3 and corresponding text for further details). On the other hand, if the user does not have a vision spot impairment in the particular eye, decision 220 branches to "No" branch 228.

A determination is made as to whether to calibrate the enhancement device for vision distortion (decision 230). For example, the user may have an impairment in on eye which distorts an image into concentric circles. If the enhancement device should be calibrated for vision distortion for the particular eye, decision 230 branches to "Yes" branch 232 whereupon vision distortion calibration occurs (pre-defined process block 235, see FIG. 4 and corresponding text for further details). On the other hand, if the user does not have a vision distortion impairment in the particular eye, decision 230 branches to "No" branch 238.

A determination is made as to whether to calibrate the enhancement device for vision color (decision 240). For example, the user may not be able to distinguish between the color green and the color yellow. If the enhancement device should be calibrated for vision color for the particular eye, decision 240 branches to "Yes" branch 242 whereupon vision color calibration occurs (pre-defined process block 245, see FIG. 5 and corresponding text for further details). On the other hand, if the user does not have a vision color impairment in the particular eye, decision 240 branches to "No" branch 248.

A determination is made as to whether to calibrate the enhancement device for vision brightness and contrast (decision 250). For example, black text displayed suddenly on a white background may irritate the user. If the enhancement device should be calibrated for vision contrast and brightness for the particular eye, decision 250 branches to "Yes" branch 252 whereupon vision brightness and contrast calibration occurs (pre-defined process block 255, see FIG. 6 and corresponding text for further details). On the other hand, if the user does not have a vision brightness or contrast impairment in the particular eye, decision 250 branches to "No" branch 258.

A determination is made as to whether to calibrate the enhancement device for vision labels (decision 260). For example, the user may have difficulty finding his car keys and wishes to configure the vision enhancement device to highlight, and optionally flash, the keys with a yellow color when they are within the viewing area of the vision enhancement device. If the enhancement device should be calibrated for vision labels for the particular eye, decision 260 branches to "Yes" branch 262 whereupon vision label calibration occurs (pre-defined process block 265, see FIG. 7 and corresponding text for further details). On the other hand, if the user does not wish to calibrate the vision enhancement device for vision labels, decision 260 branches to "No" branch 268.

A determination is made as to whether to calibrate the user's second eye (decision 270). For example, the user may have vision impairments in both eyes or the user may have a vision impairment in just one eye. If processing should calibrate the user's second eye, decision 270 branches to "Yes" branch 278 whereupon processing loops back to uncover the second eye and cover the first eye (step 280) and process calibration information for the second eye.

On the other hand, if the user does not wish to calibrate the second eye (i.e. no vision impairments) or the second eye has been calibrated, decision 270 branches to "No" branch 272. Calibration settings are applied to the vision enhancement device (pre-defined process block 290, see FIG. 8 and corresponding text for further details) and processing ends at 295.

Figure 3:
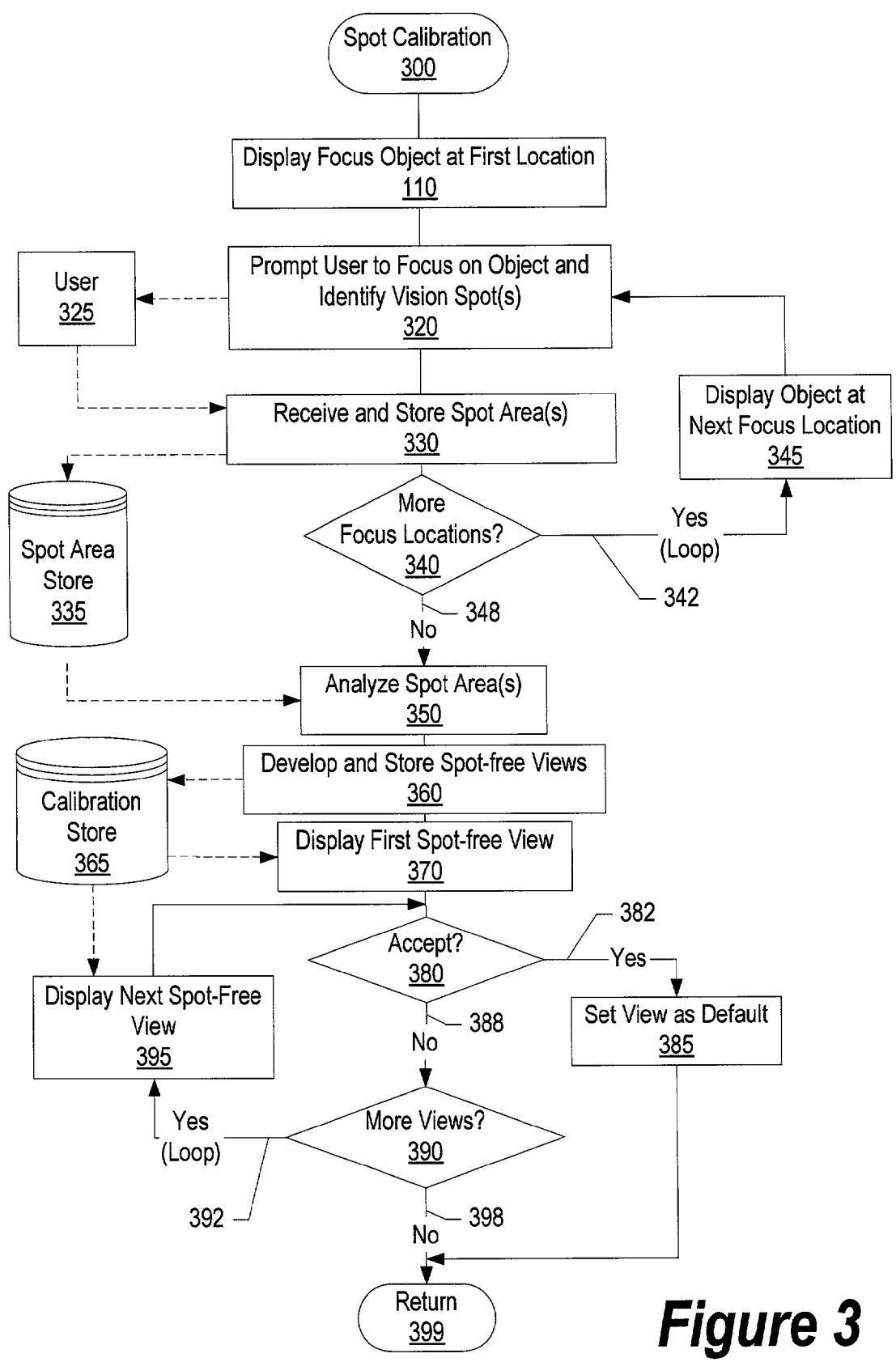
FIG. 3 is a flowchart showing steps taken in calibrating an image enhancement device to remedy vision spots.

FIG. 3 is a flowchart showing steps taken in calibrating an image enhancement device to remedy vision spots. Vision spots are "blacked-out" areas of a person's vision and typically caused by macular degeneration. Vision spot calibration starts at 300, whereupon a focus object is displayed on a screen at a first focus location. For example, a red dot may be displayed at the center of a screen for a user to focus. Processing prompts user 325 to focus on the object and identify visual spots at step 320. Using the example described above, the user may be asked to focus on the red dot in the center of the screen and trace around vision spot areas using a tracing mechanism, such as a mouse.

In one embodiment, a user may have a vision spot impairment at the center of his viewing area (e.g. the center of his retina). In this embodiment, the user may position his eye as close as possible to the center of the screen and trace around the vision spot using a mouse. The user keeps his eye in the center of the screen for each focus location (described below) in order to achieve an accurate vision spot calibration.

Processing receives vision spot area information from user 325 (step 330) and stores it in spot area store 335. Spot area store 335 may be stored on a non-volatile storage area, such as a computer hard drive. Using the example described above, processing receives information as to where the mouse traced around one or more vision spots.

A determination is made as to whether there are more locations for user 325 to focus (decision 340). In one embodiment, the user may be asked to focus on more than one area on a screen in order to perform a thorough calibration. For example, in addition to focusing on the center of the screen, the user may be asked to look at an object (red dot) at the top and bottom center of the screen, the middle left and right of the screen, and each corner of the screen. The number of focus areas may be dependent upon how detailed the user chooses to calibrate a vision enhancement device. If there are more locations for the user to focus, decision 340 branches to "Yes" branch 342 which loops back to display the focus object at the next location (step 345), and process vision spot area(s). This looping continues until there are no more locations for user 325 to focus, at which point decision 340 branches to "No" branch 348.

Processing retrieves vision spot area information from spot area store 335 and analyzes the spot areas at each focus location (step 350). This analysis is performed to ensure that each spot defect tracks with where the user is focusing. Using the example described above, if a user has a vision spot impairment on the left side of his viewing area, the vision spot should appear at the same location relative to each focus location.

Spot-free views are developed based upon the spot area analysis and stored in calibration store 365 (step 360). Calibration store 365 may be stored on a non-volatile storage area, such as a computer hard drive. Using the example described above, a view may be generated that "blacks-out" the left side of a display. A first spot-free view is retrieved from calibration store 365 and displayed for the user to view (step 370). A determination is made as to whether the user accepts the spot-free view (decision 380). If the user accepts the spot-free view, decision 380 branches to "Yes" branch 382 whereupon the spot-free view is set as the default spot-free view for the particular eye.

On the other hand, if the user does not accept the spot-free view, decision 380 branches to "No" branch 388 whereupon a determination is made as to whether there are more spot-free views in calibration store 365 (decision 390). Using the example described above, calibration store 365 may include a view that "blacks-out" the left side of the screen, and another view that "blacks-out" the upper left quadrant of the screen. If there are more spot-free views to display, decision 390 branches to "Yes" branch 392 which loops back to display (step 395) and process the next spot-free view. This looping continues until there are no more views to display, at which point decision 390 branches to "No" branch 398. Processing returns at 399.

Figure 4:
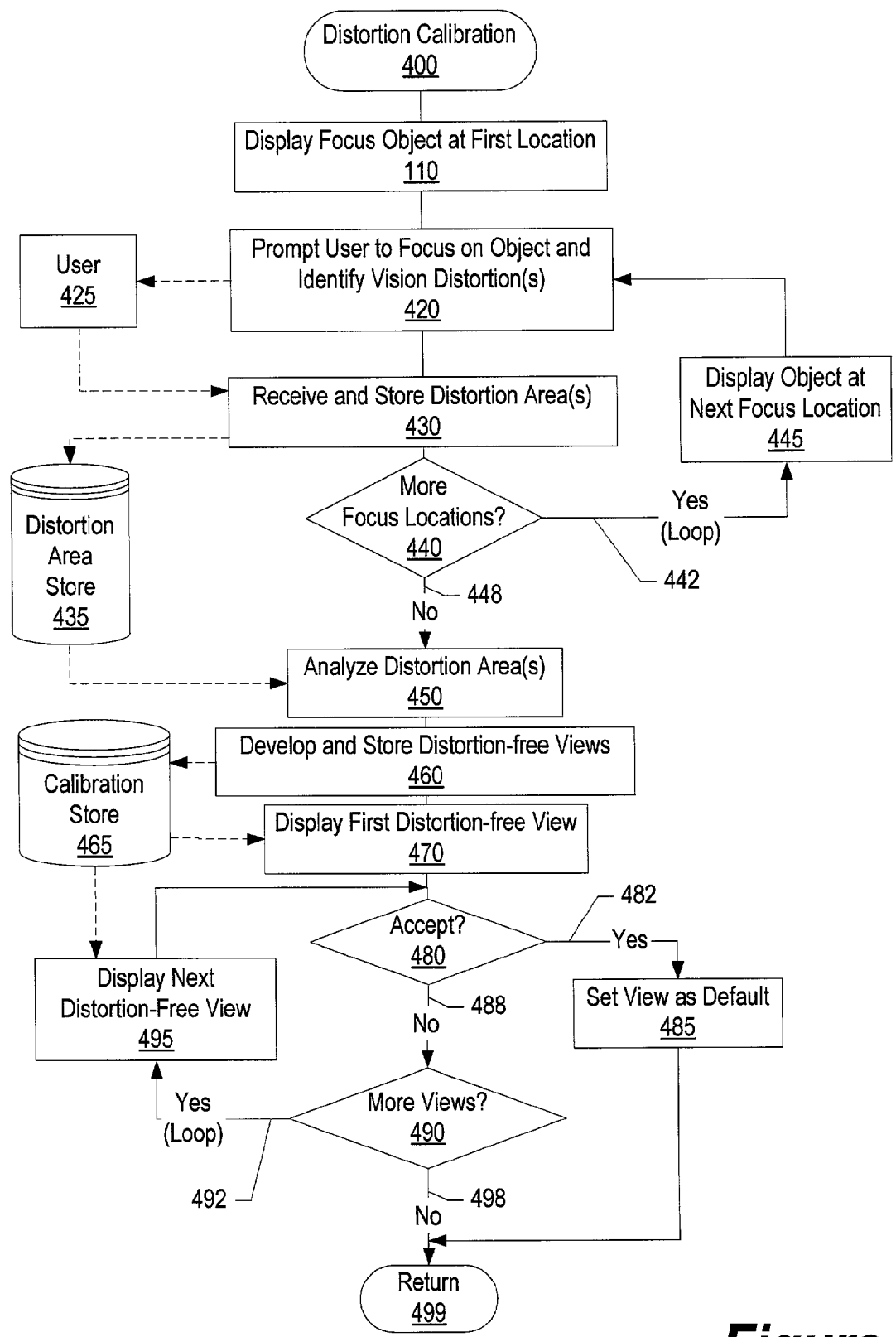
FIG. 4 is a flowchart showing steps taken in calibrating an image enhancement device to remedy vision distortion.

FIG. 4 is a flowchart showing steps taken in calibrating an image enhancement device to remedy vision distortion. Vision distortion occurs with individuals that have low vision artifacts in their eye that distort an image. For example, a person may have low vision artifacts that distort images into to concentric circles or curves. Distortion calibration starts at 400, whereupon a focus object is displayed on a screen at a first focus location. The focus object has properties such that a user is able to detect a distortion in specific areas. For example, a size configurable grid may be displayed at the center of a screen for a user to focus. Processing prompts user 425 to focus on the object and identify visual distortion(s) at step 420. Using the example described above, the user may be asked to focus on the grid and use a tracing mechanism, such as a mouse, to "click and drag" out-of-alignment grid lines into alignment.

In one embodiment, a user may also have a vision spot impairment at the center of his viewing area (e.g. the center of his retina). In this embodiment, the user may position his eye as close as possible to the center of the screen and move out-of-alignment gridlines into alignment with a mouse. The user keeps his eye in the center of the screen for each focus location (described below) in order to achieve an accurate vision distortion calibration.

Processing receives vision distortion information from user 425 (step 430) and stores it in distortion area store 435. Distortion area store 435 may be stored on a nonvolatile storage area, such as a computer hard drive. Using the example described above, processing receives information as to which gridlines were moved and to what extent.

A determination is made as to whether there are more locations for user 425 to focus (decision 440). In one embodiment, the user may be asked to look at more than one area on a screen in order to perform a thorough calibration. For example, in addition to focusing on the center of the screen, the user may be asked to look at an object (grid) at the top and bottom center of the screen, the middle left and right of the screen, and each corner of the screen. The number of focus areas may be dependent upon how detailed the user chooses to calibrate a vision enhancement device. If there are more locations for the user to focus, decision 440 branches to "Yes" branch 442 which loops back to display the focus object at the next location (step 445), and process vision distortion area(s). This looping continues until there are no more locations for user 425 to focus, at which point decision 440 branches to "No" branch 448.

Processing retrieves vision distortion area information from distortion area store 435 and analyzes the distortion areas at each focus location (step 450). This analysis is performed to ensure that each distortion defect tracks with where the user is focusing. For example, if a user has a vision distortion impairment on the left side of his viewing area, the vision distortion should appear at the same location relative to each focus location.

Distortion-free views are developed based upon the vision distortion analysis and stored in calibration store 465 (step 460). Calibration store 465 may be stored on a non-volatile storage area, such as a computer hard drive. Using the example described above, image processing may be used to generate custom alignment views that alter an image such that the image appears in alignment to the user. A first distortion-free view is retrieved from calibration store 465 and displayed for the user to view (step 470). A determination is made as to whether the user accepts the distortion-free view (decision 480). If the user accepts the distortion-free view, decision 480 branches to "Yes" branch 482 whereupon the distortion-free view is set as the default distortion-free view for the particular eye.

On the other hand, if the user does not accept the distortion-free view, decision 480 branches to "No" branch 488 whereupon a determination is made as to whether there are more distortion-free views in calibration store 465 (decision 490). Using the example described above, calibration store 465 may include a custom alignment view that alters the left side of the screen, and another custom alignment view that alters the upper left quadrant of the screen. If there are more distortion-free views to display, decision 490 branches to "Yes" branch 492 which loops back to display (step 495) and process the next distortion-free view. This looping continues until there are no more views to display, at which point decision 490 branches to "No" branch 498. Processing returns at 499.

Figure 5:
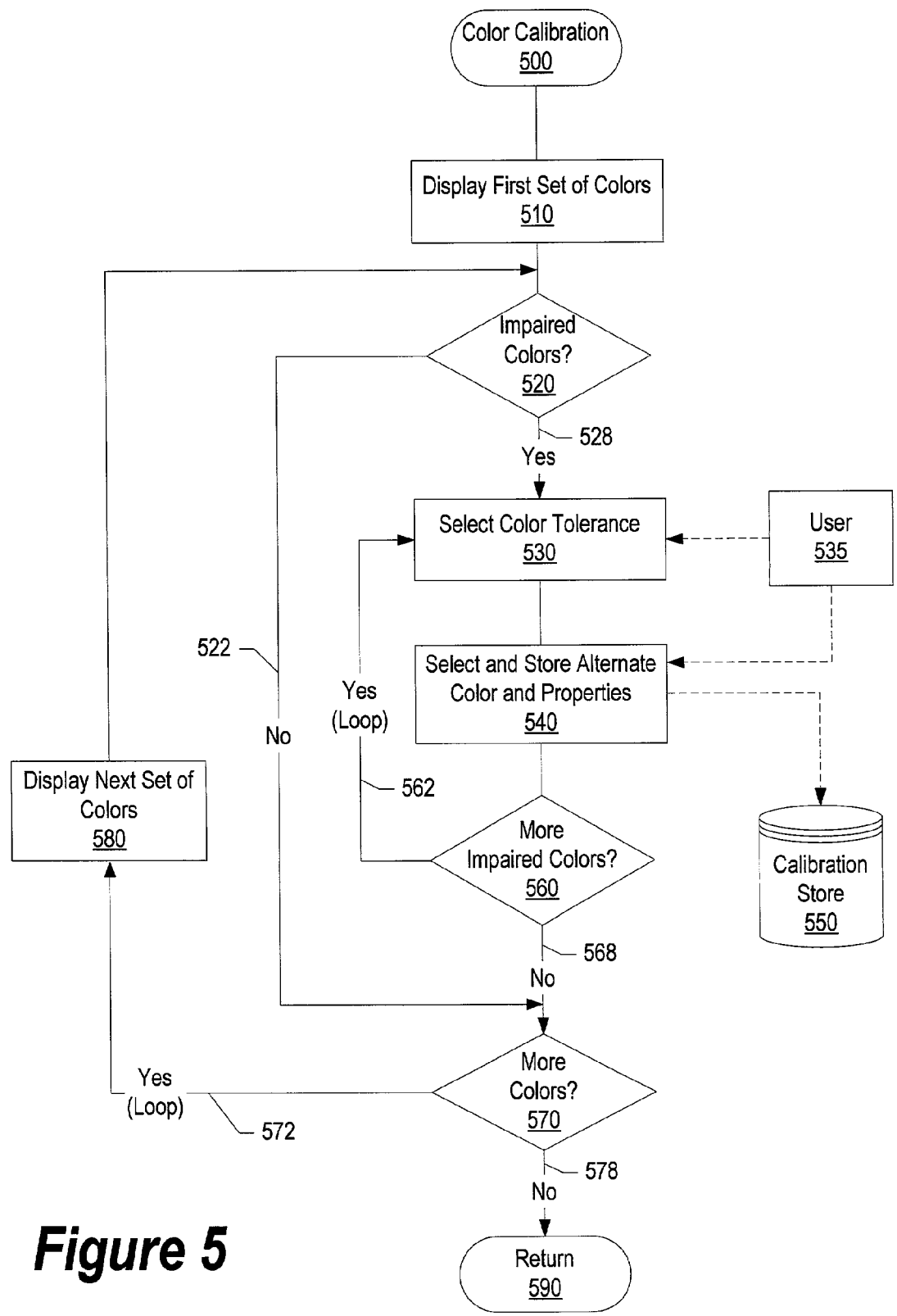
FIG. 5 is a flowchart showing steps taken in calibrating an image enhancement device to remedy vision color.

FIG. 5 is a flowchart showing steps taken in calibrating an image enhancement device to remedy vision color. Vision color, such as color blindness, is a common vision impairment among individuals. Color calibration processing commences at 500, whereupon processing displays a first set of colors. For example, the first color set may be eight colors, each displayed on a separate box, with the name of the color under each box. A determination is made as to whether the user identifies an impaired color in the color set (decision 520). Using the example described above, the user may not be able to differentiate a green block from a yellow block. If the user does not identify an impaired color in the color set, decision 520 branches to "No" branch 522 bypassing color calibration steps for the first set of colors.

On the other hand, if the user identifies an impaired color in the color set, decision 520 branches to "yes" branch 528. User 535 selects color tolerances at step 530. Using the example described above, the user may select various shades of green that he is not able to differentiate with yellow.

Processing receives user 535's alternate color properties and stores the alternate color properties in calibration store 550 (step 540). Using the example described above, the user may select a gray color flashing at one second intervals to replace the various shades of green in which the user selected. Calibration store 550 may be stored on a non-volatile storage area, such as a computer hard drive.

A determination is made as to whether the user selects more impaired colors in the first color set (decision 560). If the user identifies more impaired colors in the first color set, decision 560 branches to "Yes" branch 562 which loops back to process the next impaired color. This looping continues until the user calibrates each impaired color in the first color set, at which point decision 560 branches to "No" branch 568. A determination is made as to whether there are more colors to display (decision 570). Using the example described above, processing may have 32 sets of eight block color sets totaling 256 colors. If there are more colors to display, decision 570 branches to "Yes" branch 572 which loops back to display (step 580) and process the next set of colors. This looping continues until there are no more colors to display, at which point decision 570 branches to "No" branch 578. Processing returns at 590.

Figure 6:
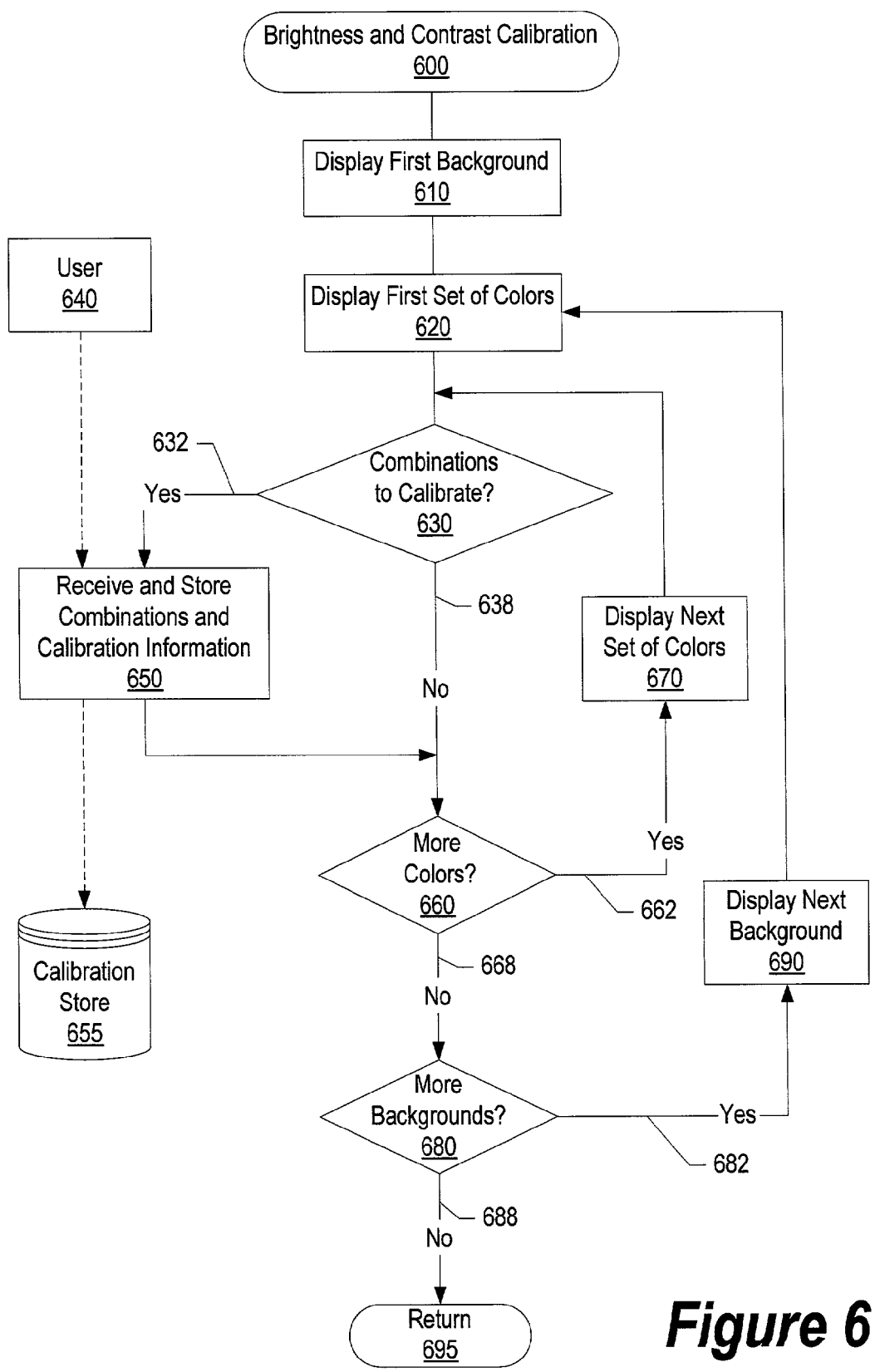
FIG. 6 is a flowchart showing steps taken in calibrating an image enhancement device to remedy vision brightness and contrast.

FIG. 6 is a flowchart showing steps taken in calibrating an image enhancement device to remedy vision brightness and contrast. Brightness and contrast calibration processing commences at 600, whereupon a first background is displayed for brightness and contrast calibration (step 610). For example, the first background may be a white background. A first set of colors is displayed on the first background in a position where the background surrounds each color for accurate contrast viewing (step 620). Using the example described above, eight boxes, each with a different color, may be displayed in a grid with spacing between each box to allow the white background to surround each box.

A determination is made as to whether user 640 chooses to calibrate one or more colors with the existing background (decision 630). Using the example describe above, the user may find the color "black" uncomfortable to view on the white background. If user 640 does not choose to calibrate one or more colors with the existing background, decision 630 branches to "No" branch 638 bypassing combination calibration steps. On the other hand, if user 640 chooses to calibrate one or more colors with the existing background, decision 630 branches to "Yes" branch 632. Processing receives user 640's calibration information and stores it in calibration store 655 (step 650). Calibration store 655 may be stored on a non-volatile storage area, such as a computer hard drive. User 640 may choose to not allow a certain color/background combination or user 640 may specify the color/background combination to transition slowly. Using the example described above, the user may choose to have processing make a slow transition, such as a three second transition, whenever processing detects black text on a white background. Another example is that when processing detects black text on a white background, processing replaces the white background with a gray background.

A determination is made as to whether there are more colors to display on the existing background (decision 660). If there are more colors to display, decision 660 branches to "Yes" branch which loops back to display (step 670) and process the next set of colors on the existing background. This looping continues until there are no more colors to display on the existing background, at which point decision 660 branches to "No" branch 668.

A determination is made as to whether there are more backgrounds to display (decision 680). Using the example described above, the next background to display may be off-white. If there are more backgrounds to display, decision 680 branches to "Yes" branch 682 which loops back to display (step 690) and process the next background. This looping continues until there are no more backgrounds to display, at which point decision 680 branches to "No" branch 688. Processing returns at 695.

Figure 7:
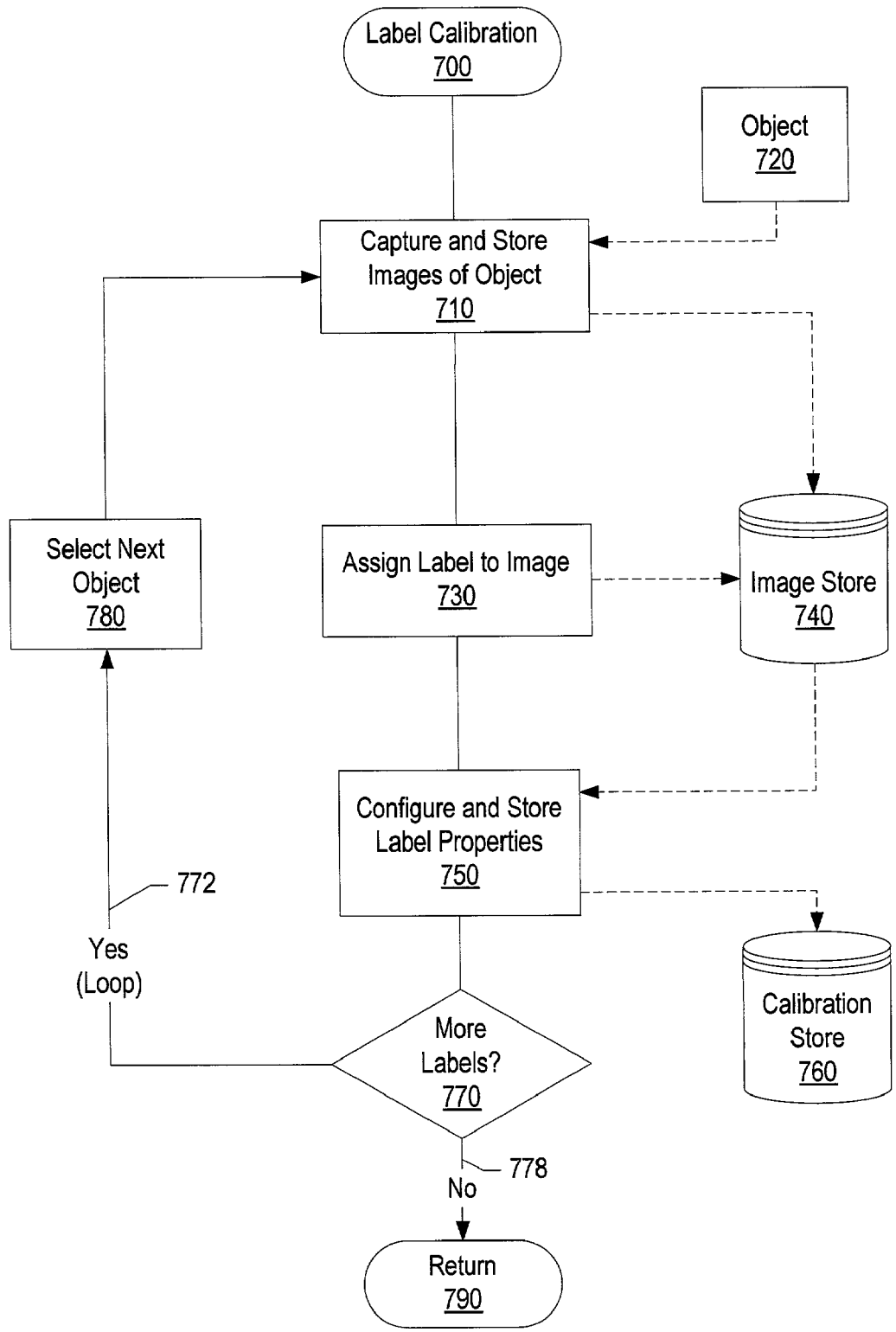
FIG. 7 is a flowchart showing steps taken in calibrating an image enhancement device to detect vision labels.

FIG. 7 is a flowchart showing steps taken in calibrating an image enhancement device to detect vision labels. Vision labels may be used to allow an image enhancement device to compare objects within a viewing area to stored images of objects. When the image enhancement device detects a match between the object within the viewing area and a stored image, the image enhancement device performs an action, such as highlighting the image in a particular color and displaying a label corresponding to the image at the bottom of the viewing area. Label calibration processing commences at 700, whereupon one or more images of object 720 are captured and stored in object store 740. Object store 740 may be stored on a non-volatile storage area, such as a computer hard drive. In order to obtain increased object recognition, multiple images (pictures) may be taken of object 720. For example, object 720 may be a user's eye doctor. Multiple pictures are taken of the eye doctor, such as eye level and both 30 profiles. A label is assigned to the image(s) at step 730. Using the example described above, the label "Eye Doctor" is assigned to the multiple images.

Label properties are configured and stored in calibration store 760 (step 750). Calibration store 760 may be stored on a non-volatile storage area, such as a computer hard drive. Label properties may include the screen location of the label when processing matches a viewed object with a stored image. In addition, label properties may include a flashing color highlighted overlaying a detected object. Using the example described above, the user may configure the "Eye Doctor" label properties such that when an image enhancement device detects the doctor is in the viewing area, the image enhancement device highlights the doctor in yellow and flashes the yellow highlight for ten seconds.

A determination is made as to whether to assign a label to more objects (decision 770). Using the example described above, the user may wish to assign a label to the eye doctor's assistant. If there are more objects to assign labels, decision 770 branches to "Yes" branch 772 whereupon the next object is selected (step 780) and processed. This looping continues until there are no more objects to assign labels, at which point decision 770 branches to "No" branch 778. Processing returns at 790.

Figure 8:
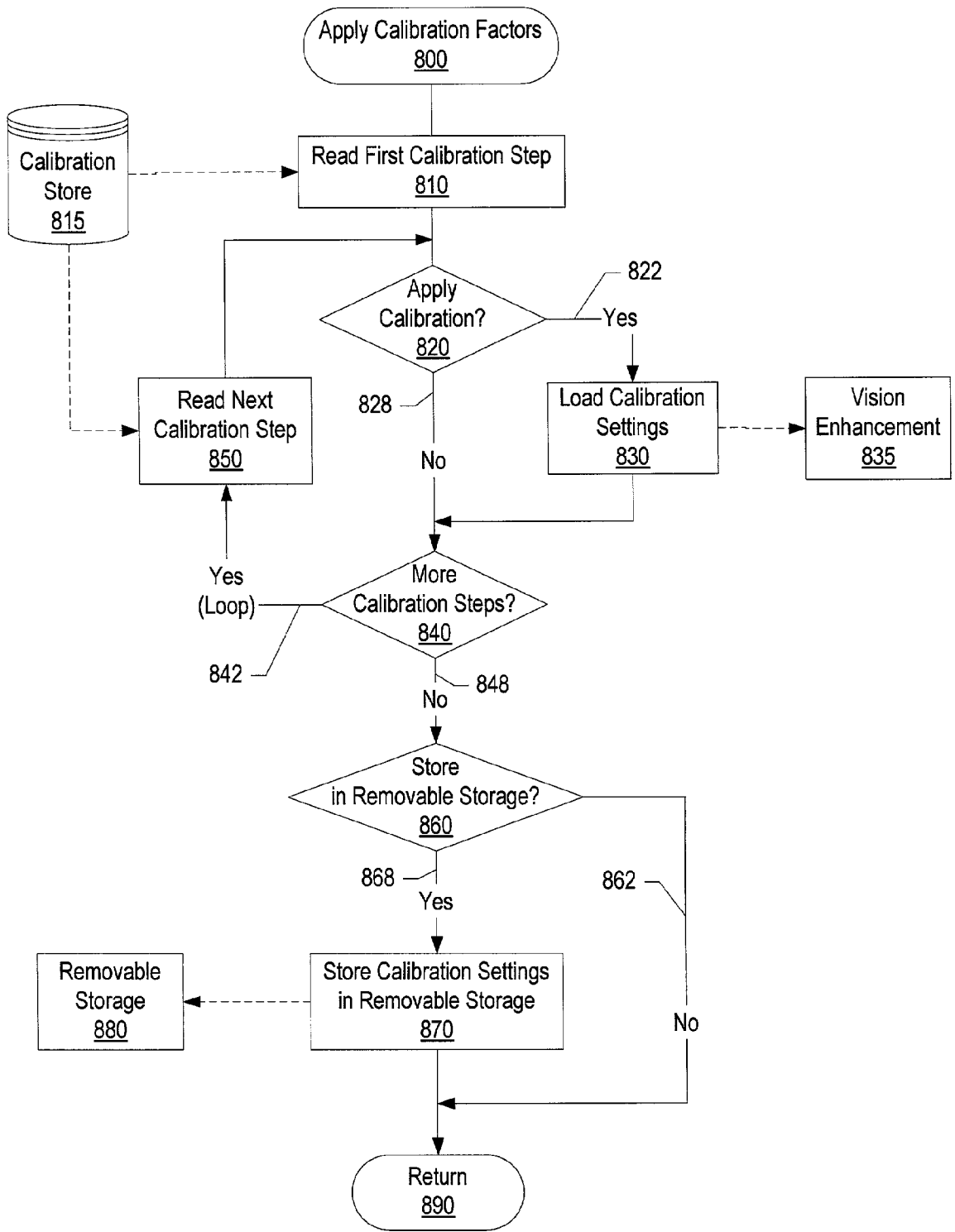
FIG. 8 is a flowchart showing steps taken in applying calibration information to an image enhancement device and storing calibration information on a portable storage device.

FIG. 8 is a flowchart showing steps taken in applying calibration information to an image enhancement device and storing calibration information on a removable storage device. Applying calibration processing commences at 800, whereupon a first calibration setting is retrieved from calibration store 815. Calibration store 815 may be stored on a non-volatile storage area, such as a computer hard drive. For example, the first calibration setting may be a spot-free view for a user's left eye (see FIG. 3 and corresponding text for further details regarding spot-free views). A determination is made as to whether to apply the calibration setting to vision enhancement 835 (decision 820). Vision enhancement 835 may be a vision correction apparatus that a person wears on his head, such as a head mounted display (HMD).

If the calibration setting should not be applied to vision enhancement 835, decision 820 branches to "No" branch 828 bypassing calibration loading settings. On the other hand, if the calibration setting should be loaded into vision enhancement 835, decision 820 branches to "Yes" branch 822 whereupon the calibration setting is loaded into vision enhancement 835 (step 830).

A determination is made as to whether there are more calibration settings in calibration store 815 (decision 840). Using the example described above, calibration store 815 may include a spot-free view for the user's left eye and a spot-free view for the user's right eye (see FIG. 3 and corresponding text for further details regarding spot-free views). If there are more calibration settings in calibration store 815, decision 840 branches to "Yes" branch 842 which loops back to retrieve (step 850) and process the next calibration setting. This looping continues until there are no more calibration settings to process, at which point decision 840 branches to "No" branch 848.

A determination is made as to whether to store the calibration settings in removable storage 880 (decision 860). Removable storage 880 may be a removable non-volatile storage device, such as a smart card or compact disk. For example, the user may wish to store his personal calibration settings on a smart card so he can load multiple vision enhancement devices using the smart card. If the user chooses not to store the calibration settings on a removable storage device, decision 860 branches to "No" branch 862. On the other hand, if the user chooses to store his calibration settings on a removable storage device, decision 860 branches to "Yes" branch 868 wherein the calibration settings are stored in removable storage 880 (step 870). Processing returns at 890.

Figure 9:
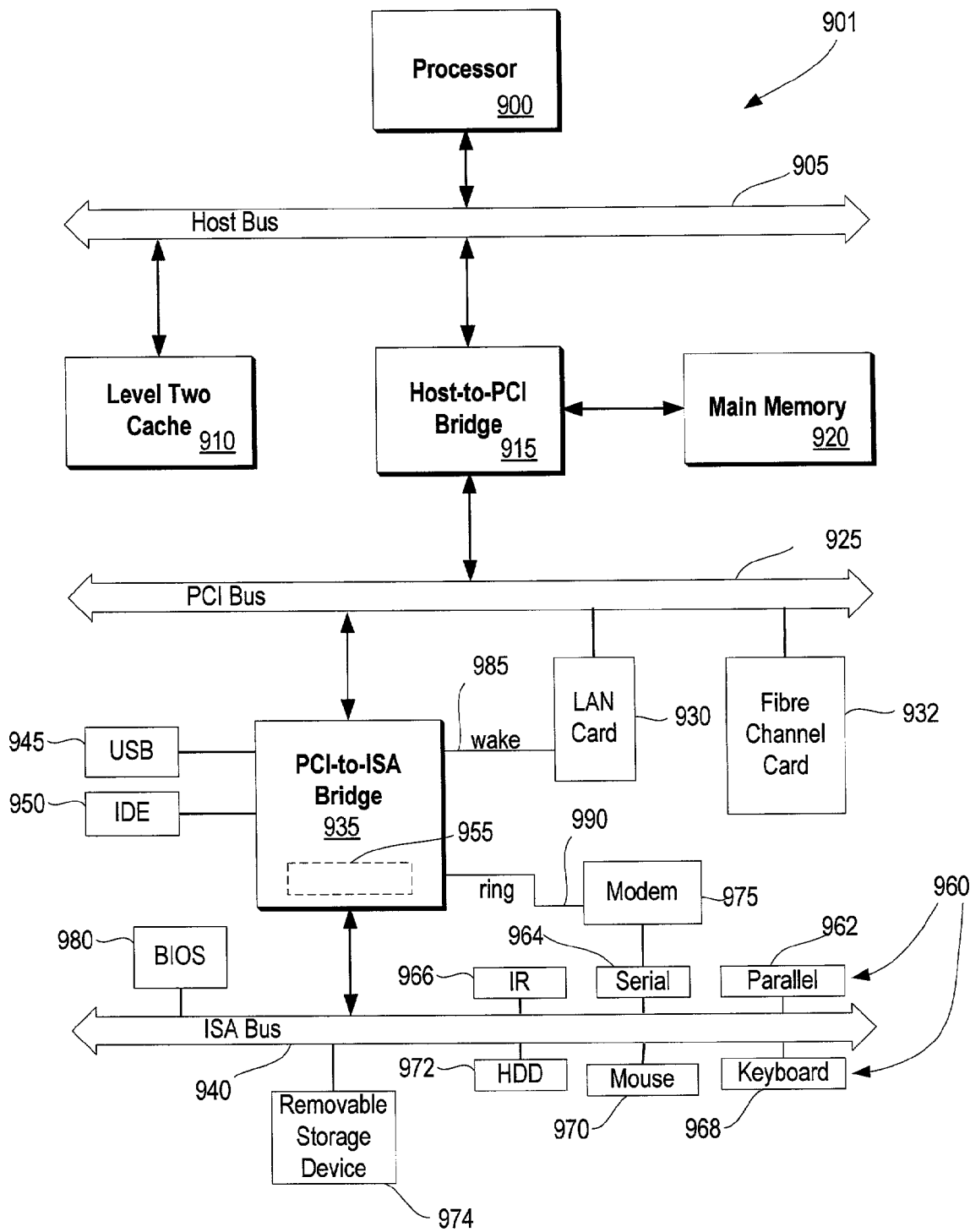
FIG. 9 is a block diagram of an information handling system capable of implementing the present invention.

FIG. 9 illustrates information handling system 901 which is a simplified example of a computer system capable of performing the invention described herein. Computer system 901 includes processor 900 which is coupled to host bus 905. A level two (L2) cache memory 910 is also coupled to the host bus 905. Host-to-PCI bridge 915 is coupled to main memory 920, includes cache memory and main memory control functions, and provides bus control to handle transfers among PCI bus 925, processor 900, L2 cache 910, main memory 920, and host bus 905. PCI bus 925 provides an interface for a variety of devices including, for example, LAN card 930. PCI-to-ISA bridge 935 provides bus control to handle transfers between PCI bus 925 and ISA bus 940, universal serial bus (USB) functionality 945, IDE device functionality 950, power management functionality 955, and can include other functional elements not shown, such as a real-time clock (RTC), DMA control, interrupt support, and system management bus support. Peripheral devices and input/output (I/O) devices can be attached to various interfaces 960 (e.g., parallel interface 962, serial interface 964, infrared (IR) interface 966, keyboard interface 968, mouse interface 970, fixed disk (HDD) 972, removable storage device 974) coupled to ISA bus 940. Alternatively, many I/O devices can be accommodated by a super I/O controller (not shown) attached to ISA bus 940. As those skilled in the art can appreciate, removable storage device 974 may be a device capable of storing information on a particular media and removing the media, such as a floppy disk drive or a smart card interface.

BIOS 980 is coupled to ISA bus 940, and incorporates the necessary processor executable code for a variety of low-level system functions and system boot functions. BIOS 980 can be stored in any computer readable medium, including magnetic storage media, optical storage media, flash memory, random access memory, read only memory, and communications media conveying signals encoding the instructions (e.g., signals from a network). In order to attach computer system 901 to another computer system to copy files over a network, LAN card 930 is coupled to PCI bus 925 and to PCI-to-ISA bridge 935. Similarly, to connect computer system 901 to an ISP to connect to the Internet using a telephone line connection, modem 975 is connected to serial port 964 and PCI-to-ISA Bridge 935.

While the computer system described in FIG. 9 is capable of executing the invention described herein, this computer system is simply one example of a computer system. Those skilled in the art will appreciate that many other computer system designs are capable of performing the invention described herein.

While this invention may be used in conjunction with traditional scanners, cameras mounted to a head mounted display (HMD), or closed circuit television (CCTV), these devices are not needed to use the calibration system and method described herein. This invention is able to calibrate any display and is not dependent on a scanner or camera to operate. For example, the calibration method may be used by a colorblind person viewing a presentation file on a notebook computer, in which case the notebook computer display is used as the display device. In addition, a television set can be calibrated using the methods provided herein, in which case the television set acts as the low vision display device.

One of the preferred implementations of the invention is an application, namely, a set of instructions (program code) in a code module which may, for example, be resident in the random access memory of the computer. Until required by the computer, the set of instructions may be stored in another computer operable memory, for example, on a hard disk drive, or in removable storage such as an optical disk (for eventual use in a CD ROM) or floppy disk (for eventual use in a floppy disk drive), or downloaded via the Internet or other computer network. Thus, the present invention may be implemented as a computer program product for use in a computer. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the required method steps.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For a non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an"; the same holds true for the use in the claims of definite articles.

What is claimed is:

1. A method for providing one or more displays to a vision impaired user, said method comprising:
    providing a calibration view to the user corresponding to the user's vision impairment;
    receiving one or more calibration inputs from the user, wherein at least one of the inputs is selected from the group consisting of a spot area, a distortion area, a color property, a color combination property, and a label property;
    creating one or more calibration settings based upon the calibration inputs, wherein the creating includes:
        providing the user with a plurality of views based upon the calibration inputs, wherein each of the views correspond to one or more calibration preview settings; and
        receiving a view selection from the user corresponding to one of the views, wherein the creating of the calibration settings includes reading the calibration preview settings corresponding to the selected view;
    generating an enhanced image based upon the calibration settings;
    displaying the enhanced image to the user;
    determining whether to calibrate a second eye;
    generating a second enhance image based upon the determination, wherein the second enhanced image is generated from performing t e providing, the receiving, and the creating separately for each of the user's eyes; and
    displaying the second enhanced image to the user.

2. The method as described in claim 1 further comprising:
    storing the calibration inputs on a removable nonvolatile storage media.

3. The method as described in claim 1 further comprising:
    receiving an image identifier selected by the user;
    acquiring an image corresponding to the image identifier; and
    applying the calibration settings to the acquired image.

4. The method as described in claim 1 further comprising:
    labeling one or more digital images, wherein the labeling includes assigning an action;
    matching a visible image to one of the labeled digital images; and
    performing the assigned action in response to the matching.

5. An information handling system comprising:
    one or more processors;
    a memory accessible by the processors;
    one or more nonvolatile storage devices accessible by the processors;
    a display accessible by the processors; and
    an image processing tool to enhance images for a vision impaired user, the image processing tool including:
        calibration view logic for providing a calibration view to the user corresponding to the user's vision impairment;
        receiving logic for receiving one or more calibration inputs from the user, wherein at least one of the inputs is selected from the group consisting of a spot area, a distortion area, a color property, a color combination property, and a label property;

calibration logic for creating one or more calibration settings based upon the calibration inputs;

a selection device accessible from the processors adapted to be manipulated by the user;

selection logic for receiving an image identifier from the user using the selection device;

image acquisition logic for acquiring an image corresponding to the image identifier;

image generation logic for generating an enhanced image based upon the calibration settings;

first display logic for displaying the enhanced image to the user on the display;

calibration application logic for applying the calibration settings to the acquired image determination logic for determining whether to calibrate a second eye;

generation logic for generating a second enhanced image based upon the determination, wherein the second enhanced image is generated from performing the providing, the receiving, and the creating separately for each of the user's eyes; and second display logic for displaying the second enhanced image to the user.

6. The information handling system as described in claim 5 further comprising:

a removable storage device accessible by the processors; and storage logic for storing the calibration inputs on the removable storage device.

7. The information handling system as described in claim 5 wherein the image processing tool further comprises:

view display logic for displaying a plurality of views to the user on the display, the views based upon the calibration inputs, wherein each of the views correspond to one or more calibration preview settings; and input logic for receiving a view selection corresponding to one of the views from the user using the selection device, wherein the calibration logic includes means for reading the calibration preview settings corresponding to the selected view.

8. The information handling system as described in claim 5 further comprising:

labeling logic for labeling one or more digital images, wherein the labeling logic includes assigning one or more actions to the digital images;

comparison logic for matching a visible image to one of the labeled digital images; and invocation logic for invoking the action corresponding to the matched digital image.

9. A computer program product stored in a computer operable media for processing images for a vision impaired user, said computer program product comprising:

means for providing a calibration view to the user corresponding to the user's vision impairment;

means for receiving one or more calibration inputs from the user, wherein at least one of the inputs is selected from the group consisting of a spot area, a distortion area, a color property, a color combination property, and a label property;

means for creating one or more calibration settings based upon the calibration inputs;

means for receiving an image identifier selected by the user;

means for acquiring an image corresponding to the image identifier;

means for applying the calibration settings to the acquired image;

means for generating an enhanced image based upon the calibration settings;

means for displaying the enhanced image to the user;

means for determining whether to calibrate a second eye;

means for generating a second enhanced image based upon the determination, wherein the second enhanced image is generated from performing the providing, the receiving, and the creating separately for each of the user's eyes; and means for displaying the second enhanced image to the user.

10. The computer program product as described in claim 9 further comprising:

means for storing the calibration inputs on a removable nonvolatile storage media.

11. The image as described in claim 9 wherein the means for creating further comprises:

means for providing the user with a plurality of views based upon the calibration inputs, wherein each of the views correspond to one or more calibration preview settings; and means for receiving a view selection from the user corresponding to one of the views, wherein the creating of the calibration settings includes reading the calibration preview settings corresponding to the selected view.

12. The computer program product as described in claim 9 further comprising:

means for labeling one or more digital images, wherein the labeling includes assigning an action;

means for matching a visible image to one of the labeled digital images; and means for performing the assigned action in response to the matching.

13. A method for providing one or more displays to a vision impaired user, said method comprising:

providing a calibration view to the user corresponding to the user's vision impairment;

receiving one or more calibration inputs from the user, wherein at least one of the inputs is selected from the group consisting of a spot area, a distortion area, a color property, a color combination property, and a label property;

creating one or more calibration settings based upon the calibration inputs;

generating an enhanced image based upon the calibration settings;

displaying the enhanced image to the user at a first image processing device;

determining whether to calibrate a second eye;

generating a second enhanced image based upon the determination, wherein the second enhanced image is generated from performing the providing, the receiving, and the creating separately for each of the user's eyes;

displaying the second enhanced image to the user at the first image processing device;

storing the calibration settings on a removable nonvolatile storage media accessible from the first image processing device;

removing the removable nonvolatile storage media from the first image processing device;

inserting the nonvolatile storage media in a second image processing device; and loading the calibration settings from the removable nonvolatile storage media into the second image processing device.

14. An information handling system comprising:

one or more processors;

a memory accessible by the processors; one or more nonvolatile storage devices accessible by the processors, at least one of the storage devices adapted to store data on removable nonvolatile storage media;

a selection device accessible from the processors adapted to be manipulated by the user;

a display accessible by the processors; and an image processing tool to enhance images for a vision impaired user, the image processing tool including:

calibration view logic for providing a calibration view to the user corresponding to the user's vision impairment;

receiving logic for receiving one or more calibration inputs from the user, wherein at least one of the inputs is selected from the group consisting of a spot area, a distortion area, a color property, a color combination property, and a label property;

view display logic for displaying a plurality of views to the user on the display, the views based upon the calibration inputs, wherein each of the views correspond to one or more calibration preview settings;

input logic for receiving a view selection corresponding to one of the views from the user using the selection device;

calibration logic for creating one or more calibration settings based upon the calibration preview settings corresponding to the selected view;

image generation logic for generating an enhanced image based upon the calibration settings;

display logic for displaying the enhanced image to the user on the display;

determination logic for determining whether to calibrate a second eye;

generation logic for generating a second enhanced image based upon the determination, wherein the second enhanced image is generated from performing the providing, the receiving, and the creating separately for each of the user's eyes;

display logic for displaying the second enhanced image to the user; and storage logic for storing the calibration settings on a removable nonvolatile storage media inserted in one of the nonvolatile storage devices.

15. A computer program product stored in a computer operable media for processing images for a vision impaired user, said computer program product comprising:

means for providing a calibration view to the user corresponding to the user's vision impairment;

means for receiving one or more calibration inputs from the user, wherein at least one of the inputs is selected from the group consisting of a spot area, a distortion area, a color property, a color combination property, and a label property;

means for creating one or more calibration settings based upon the calibration inputs;

means for generating an enhanced image based upon the calibration settings;

means for displaying the enhanced image to the user at a first image processing device;

means for determining whether to calibrate a second eye;

means for generating a second enhanced image based upon the determination, wherein the second enhanced image is generated from performing the providing, the receiving, and the creating separately for each of the user's eyes;

means for displaying the second enhanced image to the user; means for storing the calibration settings on a removable nonvolatile storage media accessible from the first image processing device;

means for removing the removable nonvolatile storage media from the first image processing device;

means for inserting the nonvolatile storage media in a second image processing device; and means for loading the calibration settings from the removable nonvolatile storage media into the second image processing device.

* * * * *